United States Patent
Martel et al.

(10) Patent No.: US 10,446,308 B2
(45) Date of Patent: Oct. 15, 2019

(54) AGGREGATION AND CONTROL OF MAGNETO-RESPONSIVE ENTITIES

(71) Applicant: POLYVALOR, LIMITED PARTNERSHIP, Montreal (CA)

(72) Inventors: Sylvain Martel, l'Île Bizard (CA); Ouajdi Felfoul, Saint-Laurent (CA)

(73) Assignee: POLYVALOR, LIMITED PARTNERSHIP, Montreal, QC (CA)

( * ) Notice: Subject to any disclaimer, the term of this patent is extended or adjusted under 35 U.S.C. 154(b) by 217 days.

(21) Appl. No.: 15/711,436

(22) Filed: Sep. 21, 2017

(65) Prior Publication Data
US 2018/0102206 A1    Apr. 12, 2018

Related U.S. Application Data

(63) Continuation of application No. 14/406,371, filed as application No. PCT/CA2012/050400 on Jun. 13, 2012, now Pat. No. 9,905,347.

(51) Int. Cl.
*A61B 17/12*    (2006.01)
*H01F 7/06*    (2006.01)
(Continued)

(52) U.S. Cl.
CPC .............. *H01F 7/064* (2013.01); *A61B 34/70* (2016.02); *A61B 34/73* (2016.02); *A61K 35/74* (2013.01);
(Continued)

(58) Field of Classification Search
CPC ........ A61K 5/00; A61K 45/00; A61K 38/164; A61K 9/5094; A61L 31/16; A61N 2/002; B82Y 25/00; A61F 2002/30079; A61F 2002/30677
USPC ................................................. 128/897, 899
See application file for complete search history.

(56) References Cited

U.S. PATENT DOCUMENTS 4,364,377 A * 12/1982 Smith .................... A61B 17/12
                                                            600/12
7,962,194 B2    6/2011 Martel et al.
(Continued)

FOREIGN PATENT DOCUMENTS

CN          100571606 C    12/2009
DE       102007028777 A1   12/2008
(Continued)

OTHER PUBLICATIONS

CA2875711 office action dated Apr. 27, 2018.

*Primary Examiner* — Samuel G Gilbert
(74) *Attorney, Agent, or Firm* — Anglehart et al.

(57) ABSTRACT

Applicants have discovered a novel apparatus and method to aggregate and displace a plurality of magneto-responsive entities (steerable self-propelled entities or SSPEs) in three dimensions using time-multiplexing. The apparatus for controlling aggregation of SSPEs in a body comprises at least three sets of magnetic field sources arranged in three axes for generating a controlled magnetic field and a controller connected to at least one of said magnetic field sources to create a three dimensional convergence point. The method for aggregating the entities can comprise using a first set and a second set of said magnetic field sources to generate opposed magnetic field gradients in each said set to cause aggregation of said magneto-responsive entities in two axes and wherein the controller is configured to reverse a direction of said magnetic field gradient in a third set of magnetic field sources in a third axis according to a first predetermined program.

9 Claims, 13 Drawing Sheets

(51) Int. Cl.
  *G01R 33/00* (2006.01)
  *A61K 35/74* (2015.01)
  *A61K 41/00* (2006.01)
  *H01F 7/02* (2006.01)
  *A61B 34/00* (2016.01)
  *A61K 47/69* (2017.01)
  *A61B 90/00* (2016.01)

(52) U.S. Cl.
  CPC .............. *A61K 41/00* (2013.01); *A61K 47/69* (2017.08); *A61K 47/6901* (2017.08); *G01R 33/0023* (2013.01); *H01F 7/0273* (2013.01); *A61B 2090/374* (2016.02)

(56) References Cited

U.S. PATENT DOCUMENTS

| | | |
|---|---|---|
| 8,961,391 B2* | 2/2015 | Deem .................. A61K 38/164 600/26 |
| 2005/0052178 A1 | 3/2005 | Ries |
| 2006/0073540 A1 | 4/2006 | Martel |
| 2006/0264690 A1 | 11/2006 | Ochi |
| 2010/0022835 A1 | 1/2010 | Kimura et al. |
| 2010/0049033 A1 | 2/2010 | Kawano et al. |
| 2010/0079142 A1 | 4/2010 | Fontius |
| 2011/0009697 A1 | 1/2011 | Kawano et al. |
| 2011/0105825 A1 | 5/2011 | Nayfach-Battilana |
| 2012/0103348 A1 | 5/2012 | Lin et al. |
| 2012/0289764 A1 | 11/2012 | Murakami et al. |
| 2013/0303948 A1* | 11/2013 | Deem .................. A61K 38/164 601/2 |

FOREIGN PATENT DOCUMENTS

| | | |
|---|---|---|
| EP | 2036483 A1 | 3/2009 |
| EP | 2090215 A1 | 8/2009 |
| JP | 2001-179700 A | 7/2001 |
| WO | WO 2005/001070 A1 | 1/2005 |
| WO | WO 2009/00047 A1 | 12/2008 |
| WO | WO 2011/049236 A1 | 4/2011 |
| WO | WO 2012/046157 A1 | 4/2012 |

\* cited by examiner

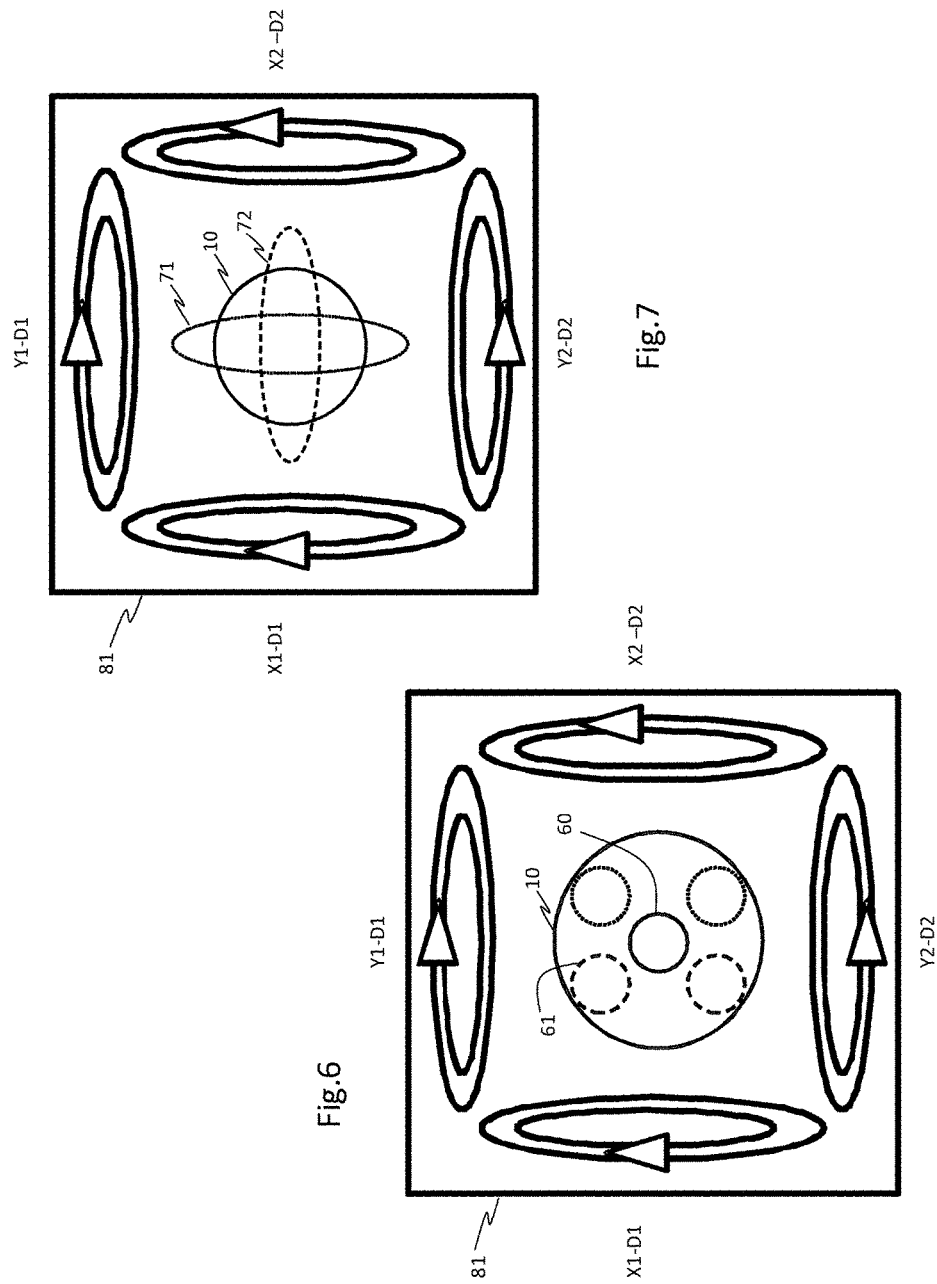

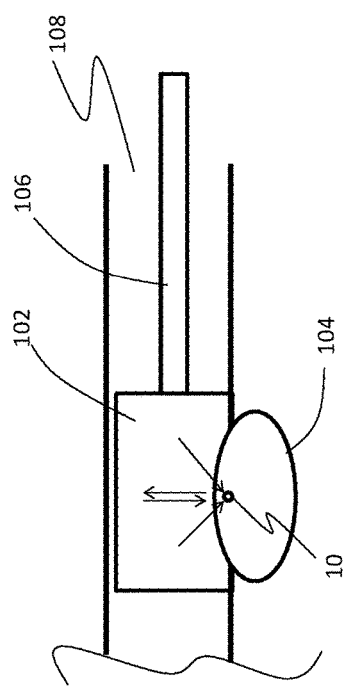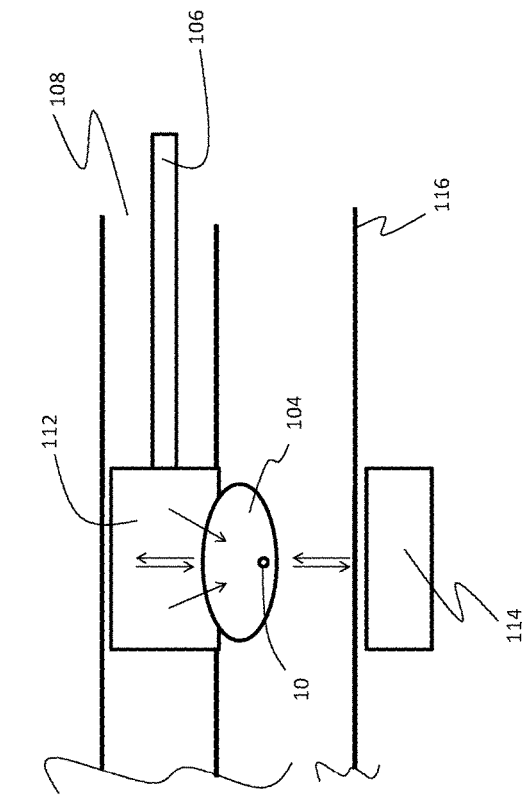

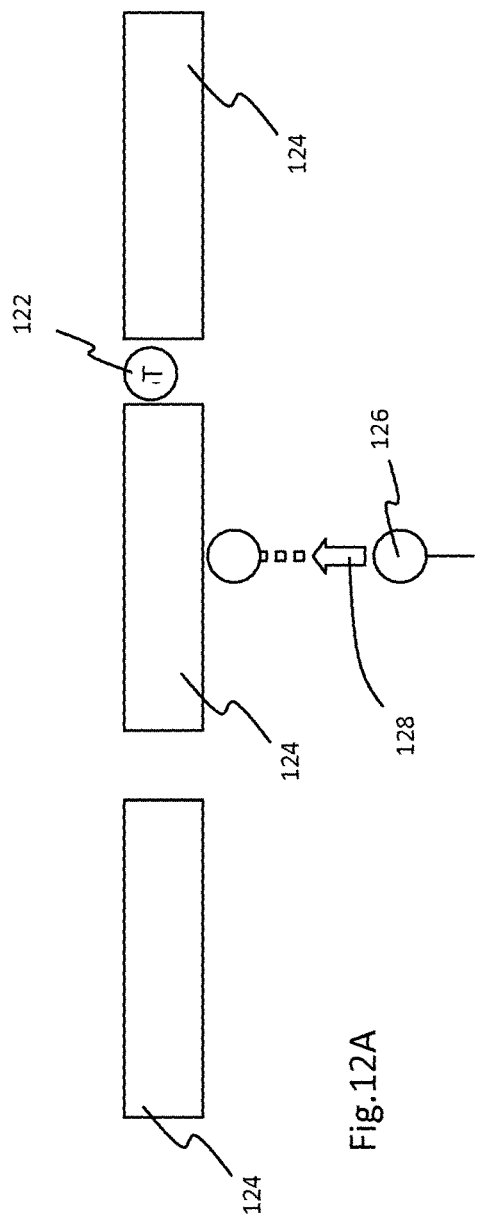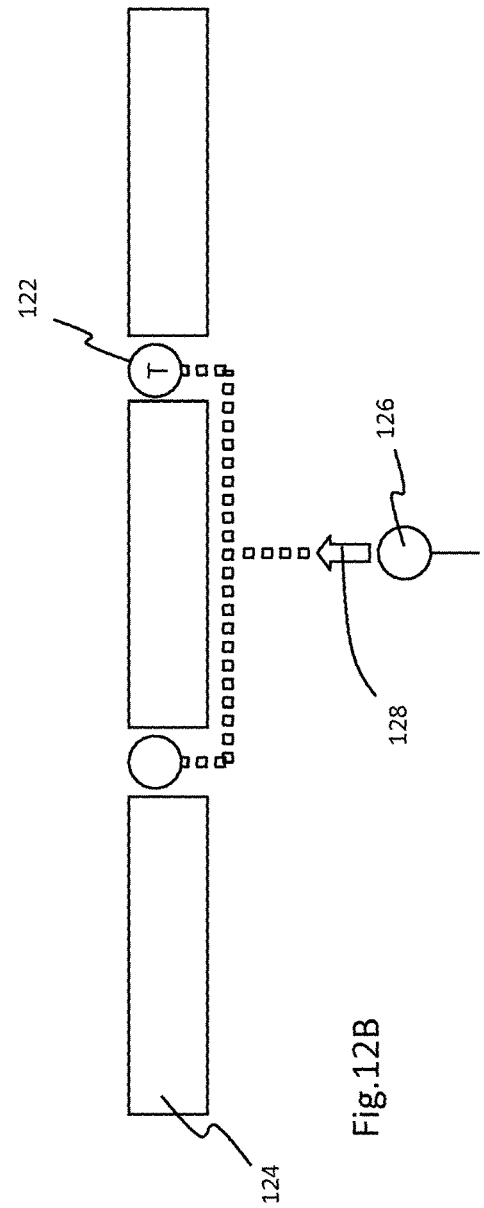

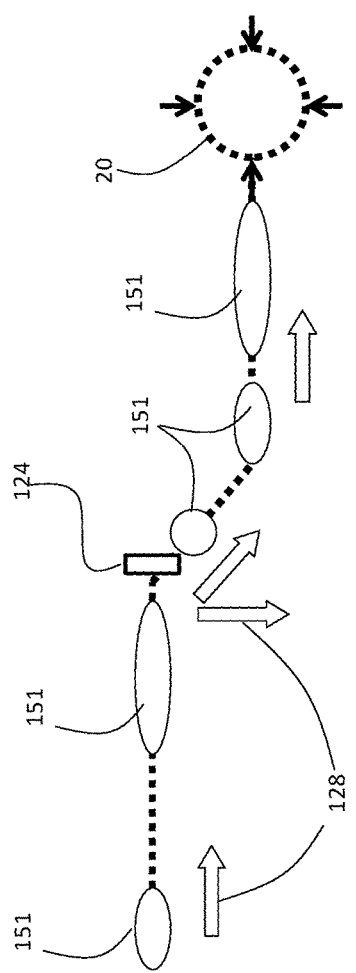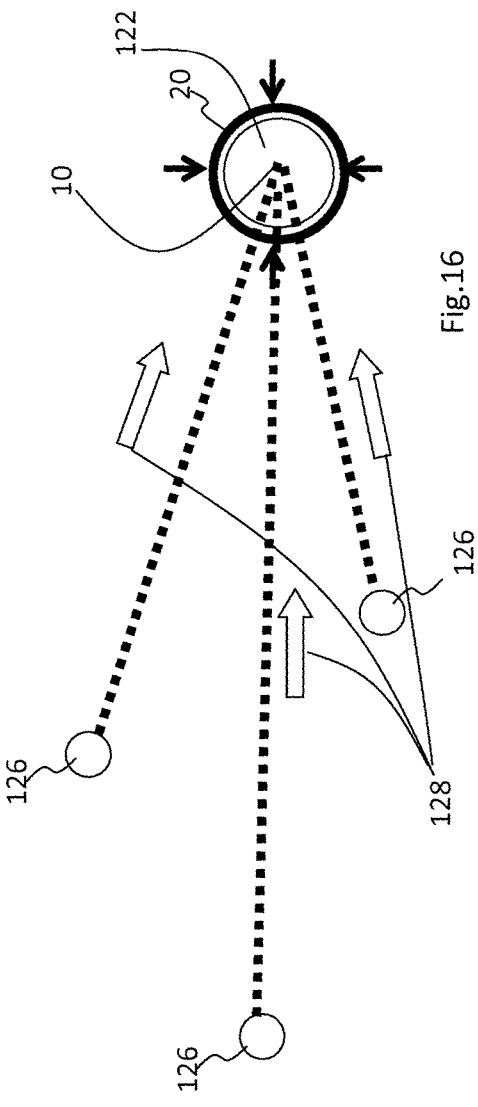

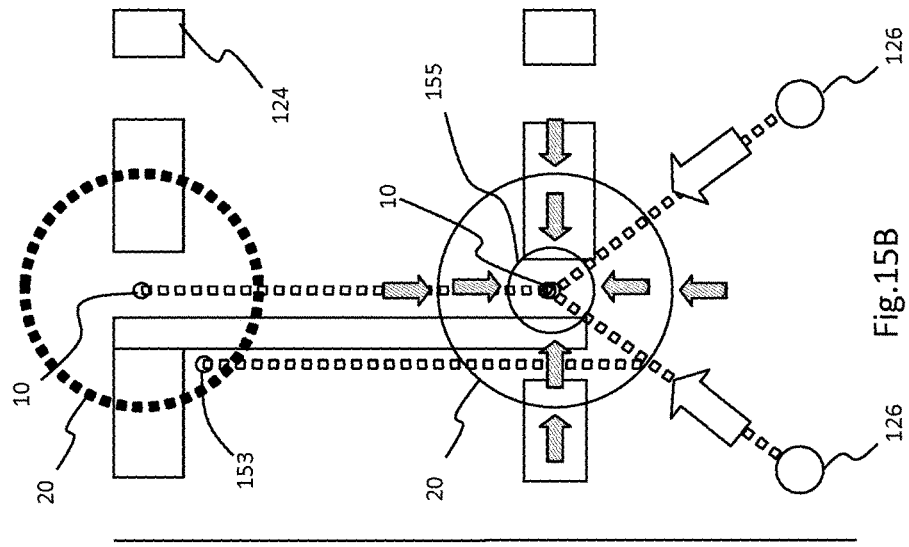
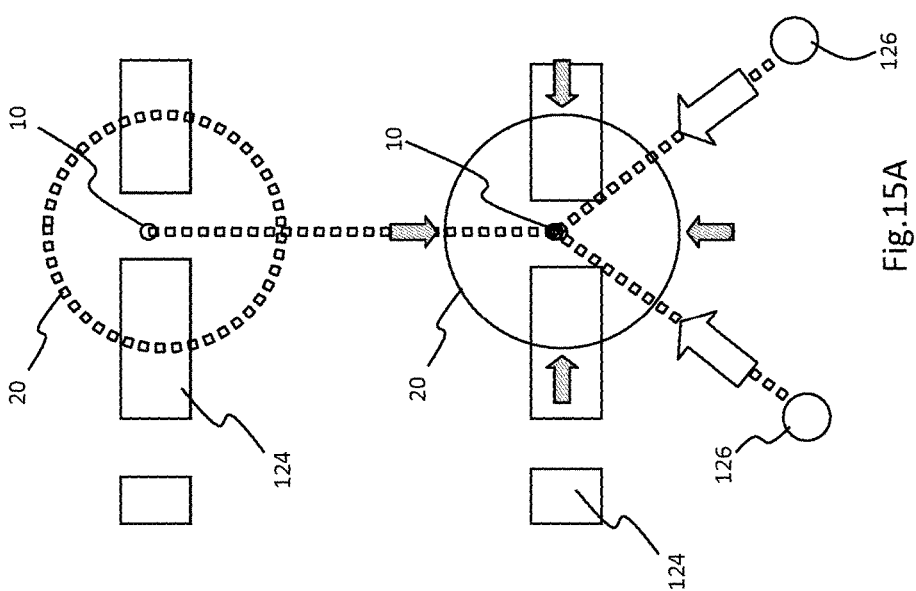

AGGREGATION AND CONTROL OF MAGNETO-RESPONSIVE ENTITIES

TECHNICAL FIELD

This invention relates generally to aggregation and control of magneto-responsive entities. More specifically, this invention relates to targeting of entities to a predetermined three dimensional convergence point by controlling magnetic fields.

BACKGROUND

Delivering therapeutic agents in vivo to a precise location using steerable entities is highly desirable in medical practice. Using magneto-responsive self-propelled entities as carriers (nano-robots or magnetotactic bacteria carriers) and direction-setting magnetic fields for carrying loads such as therapeutic agents (including radioisotopes) or diagnostic (including imaging) agents in narrowing blood vessels (such as capillaries) or in far reaching regions (e.g. the interstitial region of a tumor) is difficult, especially when operating deeper in the body to induce a propulsion (pulling) force on the carriers due to the small size of the entities (e.g. magnetic carriers) and technological limits. As such, carriers or magneto-responsive entities referred to here as Steerable Self-Propelled Entities (SSPE) are being considered to alleviate such limitations.

In a co-assigned patent by Martel et al (U.S. Pat. No. 7,962,194), ferromagnetic particles are shown to be controllably propelled by an magnetic resonance imaging (MRI) system within a patient. Martel (US Patent Application Pre-Grant Publication US2006/0073540) also teaches the directional control of micro-objects using magnetotactic bacteria in two dimensional space, such as in a petri dish. Such bacteria are self-propelled and naturally swim in the direction of the magnetic field. One of the drawbacks of the US2006/0073540 prior art is that it cannot be used to efficiently target objects in 3 dimensions, such as in large blood vessels, organs or tissues of the human body.

There is a need to increase targeting efficacy and dosage of therapeutic agents being delivered to targets in the body, while being potentially visible (detectable) with imaging modalities such as MRI. To achieve this, an aggregate of SSPEs is necessary. As such, an apparatus or system with related methods capable of aggregating SSPEs and controlling their displacement is highly desirable.

SUMMARY

Applicants have discovered a novel apparatus and method to aggregate and displace a plurality of magneto-responsive entities (steerable self-propelled entities or SSPEs) in three dimensions using time-multiplexing. The apparatus for controlling aggregation of SSPEs in a body comprises at least three sets of magnetic field sources arranged in three axes for generating a controlled magnetic field and a controller connected to at least one of the magnetic field sources to create a three dimensional convergence point. The method for aggregating the entities can comprise using a first set and a second set of the magnetic field sources to generate opposed magnetic field gradients in each the set to cause aggregation of the magneto-responsive entities in two axes and a multiplexing comprises reversing a direction of the magnetic field in a third set of magnetic field sources in a third axis according to a predetermined program.

In accordance with an embodiment of the present invention, there is provided an apparatus for controlling aggregation of magneto-responsive self-propelled entities in a body comprising at least three sets of magnetic field sources arranged in three planes for generating a magnetic field; and a controller connected to at least one of the magnetic field sources to create a three dimensional convergence point.

In some embodiments, a first set and a second set of the magnetic field sources generate an opposed magnetic field gradients in each the set to cause aggregation of the magneto-responsive entities in two axes and wherein the controller is configured to reverse a direction of the magnetic field in a third set of magnetic field sources in a third axis according to a first predetermined program, where the magnetic field sources in the third axis further comprise two coils wired for current flow in a same direction.

In some embodiments, the controller is configured for sequentially actuating all combinations of two sets of magnetic field sources according to a second predetermined program. In other embodiments, at least one magnetic field source is located outside the body and comprises permanent magnets.

In accordance with another embodiment of the present invention, there is provided an apparatus having a controller configured for targeting the entities to a location in the body by moving the convergence point with respect to the sets of magnetic field sources. In other embodiments, the convergence point is moved using a position device for moving the magnetic field sources. In other embodiments, the convergence point is moved by moving a platform upon which rests a body.

In accordance with another embodiment of the present invention, there is provided an apparatus where the magneto-responsive entities comprise magnetotactic bacteria and wherein the second predetermined program provides a frequency at which a predetermined proportion of the magnetotactic bacteria are able to realign to the field following change in the magnetic field.

In accordance with yet another embodiment of the present invention, there is provided an apparatus wherein the controller is configured to change a size or shape of the convergence point (amplitude modulation to increase or decrease the aggregation zone) to increase pathfinding capability of magneto-responsive entities.

In accordance with still another embodiment of the present invention, there is provided an apparatus having a magneto-responsive entity detector (such as an MRI machine) for detecting the location of the magneto-responsive entities. In such an embodiment the apparatus can further comprise a platform for moving between a first station having the magneto-responsive entity detection device and a second station having the magnetic field sources.

In accordance with yet still another embodiment of the present invention, there is provided a method of aggregating magneto-responsive self-propelled entities in a body comprising: generating in the body a magnetic field having a three dimensional convergence point; and allowing the entities to move toward and aggregate near the convergence point. In such embodiments, a constant magnetic field gradient can be maintained in two axes while alternating a direction of the magnetic field in a third axis according to a predetermined program.

In some embodiments, the method further comprises sequentially actuating all combinations of two opposed magnetic field sources according to a predetermined program.

It is physically impossible to concentrate all lines of a static magnetic field to a single point in 3D space without an obstacle or surface. However, Applicants have discovered that SSPE's can be forced towards a single point to create an aggregate of SSPE's by changing at least one axis in a time multiplexed fashion. A three dimensional convergence point (CP) in a magnetic field is a point, unbounded in space, to which the entities following the direction of the magnetic field in an aggregation zone (AZ) will move to and aggregate. The magnetic field at the convergence point is effectively zero and surrounding the convergence point in the AZ, the effective field points from all directions to the convergence point. Because a magnetic field is not a point source, at least one of the magnetic field sources will be time varied to cause the entities to move toward the convergence point and stay close to the convergence point.

Therefore, maintaining any two axes (x, y or z) with a constant (static) magnetic field and changing the direction of the other axis depending upon the other two axes being maintained constant will generate a convergence point. Similarly, maintaining one axis constant and changing the direction of the other two axes in a time multiplex-fashion at the same time (synchronized) or with a phase (delay) will function to generate a convergence point, provided that, when the SSPE is a magnetotactic bacteria, the change is done at a frequency that allows for appropriate reaction of the SSPE, such as between 0.1 and 5 Hz or preferably about 0.5 Hz. The direction of all three axes can be changed in a time multiplexing fashion simultaneously or with a delay between each axis. All combinations are possible provided that the magnetic field gradient of at least one axis (x, y or z) changes direction in a time multiplexed fashion with a switching speed appropriate with the reaction time of the SSPE.

BRIEF DESCRIPTION OF THE DRAWINGS

The invention will be better understood by way of the following detailed description of embodiments of the invention with reference to the appended drawings, in which:

FIG. 6 is a schematic representation of various modulation modes for increased pathfinding capability.

FIG. 7 is a schematic representation of various modulation modes for increased pathfinding capability.

FIG. 10 is a schematic representation of a portable configuration having one internal magnetic field source that is configured to "encircle" a convergence point for aggregating and controlling magneto-responsive entities.

FIG. 11 is a schematic representation of a hybrid configuration having one internal and one external magnetic field source for aggregating and controlling magneto-responsive entities.

FIG. 12 is a highly schematic representation of a non-pathfinding entity (FIG. 12A) and a pathfinding entity (FIG. 12B).

FIG. 14 is a highly schematic representation of a directional mode (D-mode) control of magneto-responsive entities where the arrows represent the general direction of the magnetic field gradient.

FIG. 15 is a highly schematic representation of using the aggregation mode for targeting purpose (FIG. 15A); highlighting an example where a reduction of the aggregation zone (or convergence point size) is used to enhance the efficacy in targeting (FIG. 15B).

FIG. 16 (appearing on same sheet as FIG. 14) is a schematic representation of an aggregation target mode (T-mode) control of magneto-responsive entities.

FIG. 19 is a graphical representation of time-multiplexing in opposing sets of coils arranged in the X, Y and Z axes, where

DETAILED DESCRIPTION

Steerable Self-Propelled Entities (SSPE) or magneto-responsive entities are defined here as untethered entities where the source of propulsion or the system responsible for the displacement of the entity is part of, attached to, or embedded in the entity itself. Steerable self-propelled entities include a group of objects or microorganisms and any biological system or hybrid system including micro- and nano-systems or structures made of biological and/or synthetic (including chemical, artificial, etc.) materials and/or components where the directional motion can be influenced by inducing a torque from a directional magnetic (e.g. from a permanent magnet) or electro-magnetic field (magnetic field includes here electro-magnetic field generated by an electrical current flowing in a conductor), a method referred to here as magnetotaxis where the direction of motion of such SSPE is influenced by a directional magnetic field (the SSPE can also be functionalized and be attached to other structures if required). Examples of such SSPE include but are not limited to a single or a group (swarm, agglomeration, aggregate, etc.) of flagellated Magnetotactic Bacteria (MTB), or other bacteria or other microorganisms capable of self-propulsion and influenced for the purpose of directional control by a directional magnetic field that could have been modified previously accordingly from various methods including but not limited to cultivation parameters, genetics, or attached, embedded to other entities modified to allow control (in this document the word "control" means influence on the movement, displacement, behavioural motion, etc., of the entity) by magnetotaxis such as other cells (including red blood cells), or attached to a synthetic structure that can be influenced by a directional magnetic field or gradient, or by adding micro- or nano-components to the bacteria, cells, or other microorganisms to make the directional motion of the implementation including hybrid (made of biological and synthetic components) implementation sensitive to magnetotaxis or a directional magnetic field such as the one capable of influencing the direction of a magnetic nano-compass needle.

As minimum requirements, each SSPE must have an embedded propulsion system and an embedded steering system. The steering system must be conceived in a manner that it can be influenced by a torque induced from directional magnetic field lines (magnetotaxis control) generated by an appropriate coil (or permanent magnets) configuration (part of the magnetotaxis system).

The magnetotactic bacteria of type MC-1 is an example of a biological SSPE where the flagella bundles are the propulsion (propulsive) system and the chain of membrane-based nanoparticles (crystals) known as magnetosomes embedded in the cell implements such steering system by acting like a miniature magnetic compass needle that can be oriented with a directional magnetic field.

Figure 1:
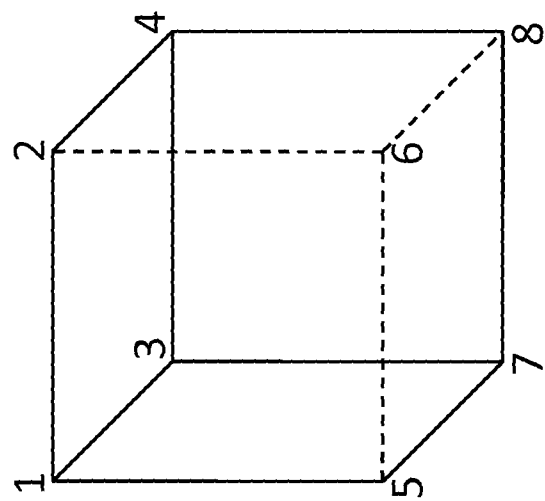
FIG. 1 is an illustration of a magnetotactic bacterium (magneto-responsive entity) according to an embodiment of the present invention.

FIG. 1 shows a schematic representation of an MC-1 magnetotactic bacterium 13 acting as a natural SSPE (or magneto-responsive entity) with the two flagella 12 and a chain of magnetosomes 14 used for propulsion and steering, respectively. The magnetosome 14 allows to orient the bacterium 13 with magnetic field line in order to seek a pole 16 such that combination of the orientation and propulsion will lead the bacteria toward that pole 16.

Fundamental Principle and Main Motivation. The main motivation behind the magnetotaxis system is to use magnetic field mainly for directional control (without motivation for inducing a displacement force to navigable entities). As such, the system is designed primarily for SSPEs as defined here. The fact that the magnetic field from the magnetotaxis system is only intended for directional control and not to provide a propelling or pulling force (although a small if not negligible pulling force may be present), translates into the need for a much lower magnitude (intensity) of magnetic field which makes the navigation of smaller SSPE, technologically possible using much less power.

Indeed, here directional control is performed by inducing a directional torque T by applying a directional magnetic field B as described by the following equation:

$$\vec{T} = V \cdot \vec{M} \times \vec{B}. \quad (1)$$

Since for an entity with the same volume and magnetization, the magnitude of the magnetic field required is much less for generating a directional torque compared to a directional displacement (pulling) force, directional control of such entity capable of providing its own propulsion (propelling) force would require significantly less power when operating in similar environments (conditions).

With a special coil configuration and combinations of various directional electrical current intensities flowing through each coil, it is possible to not only perform directional control of the SSPEs but also to aggregate them by performing directional control on the SSPEs toward a specific "central" location (that could be offset towards a desired direction). This capability of aggregating the SSPEs is very important yet critical for many interventions. For drug delivery to a tumor for instance, the overall size of each SSPE must be reduced to allow them to travel in the microvasculature or small openings. With SSPEs having such small overall size, the amount of therapeutics being carried by each SSPE is also reduced. As such, controlling an aggregate of SSPE would allow us in this particular type of intervention, to deliver a larger and potentially a sufficient dose of therapeutic agents. Another reason for such a system to have the capability to aggregate SSPE is to prevent a dispersion of the SSPEs. Indeed, with the coils outside the patient, it is not possible to perform individual control on each SSPE simultaneously but rather on the whole group. Hence, when using a system designed with only directional control without the capability to aggregate SSPEs, the initial grouping would typically spread due to variation of velocity among the SSPEs and/or when subjected to other perturbations or forces acting differently on each SSPE. Such spreading would not only reduce the density of the aggregate making MR-detection/tracking more difficult to impossible, but would result in loosing many SSPEs when the size of the dispersion would extend beyond the length of the distance between successive bifurcations leading to different targets for example, considering the fact that directional control in this particular case can only be performed on the whole group within the control range of the magnetotaxis system.

Basic Configurations and Principle of the Magnetotaxis System. A magnetotaxis system can take the form of a platform, a portable system or tool, or be a hybrid version. A magnetotaxis system as a platform is designed to surround all or a part of the patient's body, i.e. that the patient or part of the body to be treated can be placed inside the inner diameter of the magnetotaxis system. A portable system is one where the inner diameter of the system such as the coil configuration does not surround the patient or the part of the body to be treated but instead the region to be treated. In other words, the magnetic source configuration is designed to be applied directly to the targeted site to be treated. As such, the targeted site must be physically accessible by the magnetotaxis system. Examples are rectal tumors accessible through the rectum or any regions in the body being accessible through open surgery or by other techniques including non-invasive approaches such as laparoscopy. The hybrid type is any combinations of the previous two types.

Although several configurations could be envisioned for the sources of magnetic field, the important aspect to consider is that a given configuration must besides directional control through magnetotaxis, also have the capability to aggregate the SSPEs using a magnetic field that can be focused within a 3D space toward a target.

For instance, for a focused magnetic gradient field generated by magnetic coils powered by opposed currents for example, would result in the direction of the magnetic field to always point to a location determined by the values of the electrical current circulating in each coil. Therefore, SSPEs such as Magnetotactic Bacteria (MTB) that naturally follow the magnetic field direction will be guided toward this location.

The size of the targeted region depends on the intensity of the current circulating in the coils and the sensitivity of the SSPE to the direction of magnetic field generated by the coils of the magnetotaxis system. For instance, MTB of type MC-1 are sensitive to very weak magnetic fields. We estimated the magnetic sensitivity by counting the number of bacteria as a function of a spatially variable magnetic gradient field. The MTB are found to distribute inside a 0.3 Gauss magnetic equipotential circle, with nearly half of them inside the 0.1 Gauss magnetic equipotential (not shown). As such beside increasing or decreasing the current circulating in the coils to modify the size of the AZ, the outer limit of the AZ can be arbitrarily selected at any equipotential (e.g. 0.1 or 0.3 Gauss) depending on a satisfactory percentage of MTB in the AZ or target zone (unless a pre-selection of MTB's has been done).

MC-1 magnetotactic bacteria spatially distribute within magnetic equipotential zones and there is normal variation in magnetotaxis sensitivity among the MTB. A magnetic guidance system capable of directing the SSPE toward a convergence point and referred to here as a magnetotaxis system is required. A simple electromagnet can be used to achieve that task; however the convergence point or targeting point would be limited to the region on the surface (closer to the source of magnetic field) while not being capable of locating the convergence point towards deep organs or regions. Using a magnetotaxis system based on 3D magnetic coils allows for targeting SSPE in deep targeted regions by choosing the plane on which the SSPE will converge.

Figure 2B:
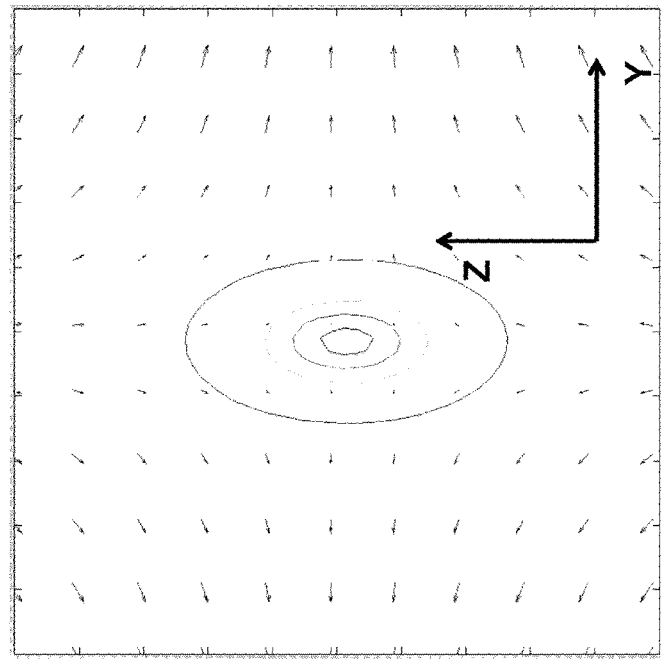
FIG. 2 is a graphical representation of the magnetic fields in the X-Z plane (FIG. 2A) and Y-Z plane (FIG. 2B) where the magnitude of the field is proportional to the length of the arrow.
Figure 2A:
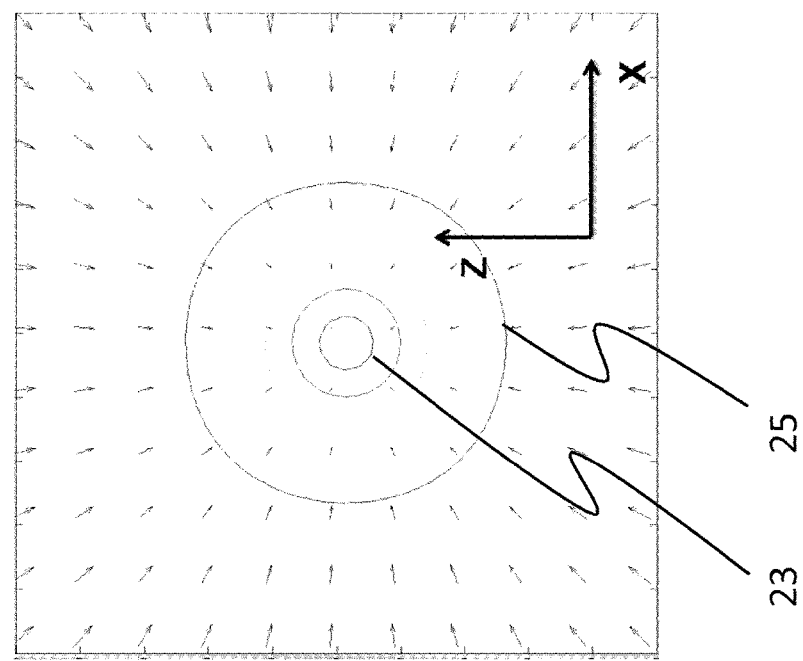

FIG. 2A shows the direction of the magnetic field in the x-z plane and FIG. 2B shows the y-z plane (the magnitude of the field is proportional to the length of the arrows). Although the magnetic field converges in a single point in the x-z plane shown in FIG. 2a, it does not converge to a single point in a 3D space but rather to a 2D convergence area 23 in a 2D aggregation area 25. In fact, a y-component (used as the referential in FIG. 2b) of the magnetic field is present, and it becomes more important near the convergence point. Notice the direction of the arrows (representing the magnetic field direction and thus the direction of the SSPE) that point to the outside in FIG. 2b. FIG. 2 suggests that a static magnetic field would not result in 3D targeting of SSPE. Therefore, an adequate coil configuration with time-multiplexing where the magnetic field is reversed back-and-forth at a specified frequency is required. Integrating this technique into the magnetotaxis system where targeting is performed with such focused magnetic field is then equivalent in functionality to having an electromagnetic tip you can use in any plane (and not only at the surface closer to the tip) and deeper inside the body where positioning the tip is not possible.

This approach leads to some fundamental observations for potential hardware configurations of coils for magnetotaxis systems. Using four coils, a mathematical relationship exists between the electrical current in each coils powered with reversed currents in the two coils of each pair and the position of the convergence point. By using six coils, the two additional coils can minimize the y-component (see FIG. 2b) of the field for better controllability in 3D space. Instead of changing the current on the coils that generate the gradient field, a set of Helmholtz coils can be used to change the position of the convergence point. The advantage of this setup is that the gradient will be always the same (or approximately the same) which is not possible with the other configuration. The configuration with Helmholtz coils is more complex but if it is important that the gradient remain always the same (or approximately the same), then it can be a valuable alternative.

Focused magnetic field pointing to the center also denoted here the Convergence Point. The arrows indicate the direction of the magnetic field. As shown, the magnitude of the magnetic field represented by the length of the arrows, decreases toward the convergence point or away from the coils used to generate the magnetic field. The circles around the convergence point denotes the outer limit of the AZ which can be adjusted by adjusting the intensity of the current circulating in the coils, i.e. larger currents would typically result into smaller AZ.

Main Fundamental Configurations. A simple example of a configuration for the magnetotaxis system consists of two sets of coils, where one set is used to aggregate the SSPE while the other set of coils is used to move the same aggregate in a given direction. However, more complex or simpler configurations are also possible.

Figure 3:
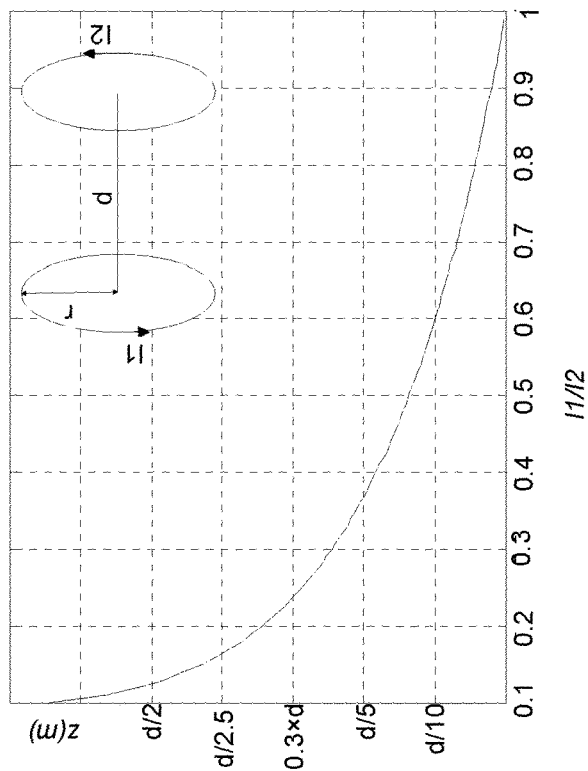
FIG. 3 is a graphical representation showing the distance of a convergence point from a center point between two opposing coils as a function of current ratio in the Maxwell coils.

FIG. 3 shows that changing the current value for one coil of a Maxwell pair causes the position of the magnetic field convergence point to move from the center. However, the gradient linearity is no longer preserved.

Indeed, although many variances are possible, one basic possible implementation relies on a 3-axis Maxwell coil configuration (ref.: M (Maxwell) configuration). The Maxwell configuration causes the SSPE that follow the magnetic field lines to be trapped in the center of the coil configuration. Controlling the motion of the SSPE is achieved by changing the current ratio between the coils of the same pair. Since the current flowing in each coil of a Maxwell pair should be the same in order to have a linear gradient, having different current in each coil of the same pair will then lead to a non-linear gradient. The relationship between the ratio of I1 and I2 (current in each coil of a Maxwell pair) and the position of the zero magnetic fields also referred to as the magnetic field convergence point is plotted in FIG. 3.

Depending on the displacement side, although the current values can be changed in several ways, in one simple approach, one current value is set to the maximum while the other is changed according to the desired position. The mathematical relationship between the convergence point position and the current ratio is given by $$I = \frac{I1}{I2} = \sqrt{\frac{r^2 + \left(z + \frac{d}{2}\right)^2}{r^2 + \left(z - \frac{d}{2}\right)^2}}^{-3} \tag{2}$$

where I1(A) and I2(A) are current in each coil of the Maxwell pair, r(m) is the radius of the coil, d(m) is the distance between the coils and z(m) is the required position.

Figure 4B:
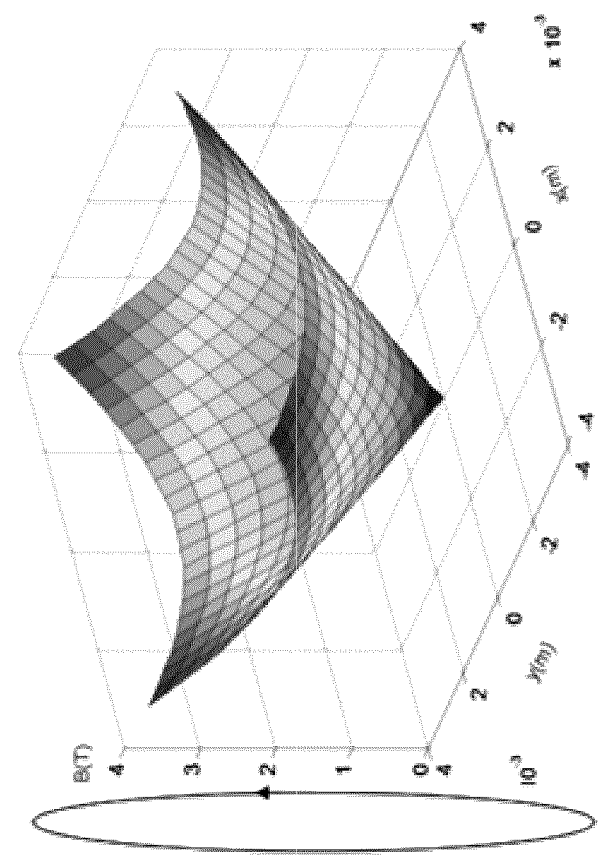
As shown in FIG. 4B, the magnetic field lines are strongest at the 4 top (dark) edges and the gradient is directed toward the center (the convergence point, darker area at bottom) where the field intensity is (near) zero (toward a minimum value).
Figure 4A:
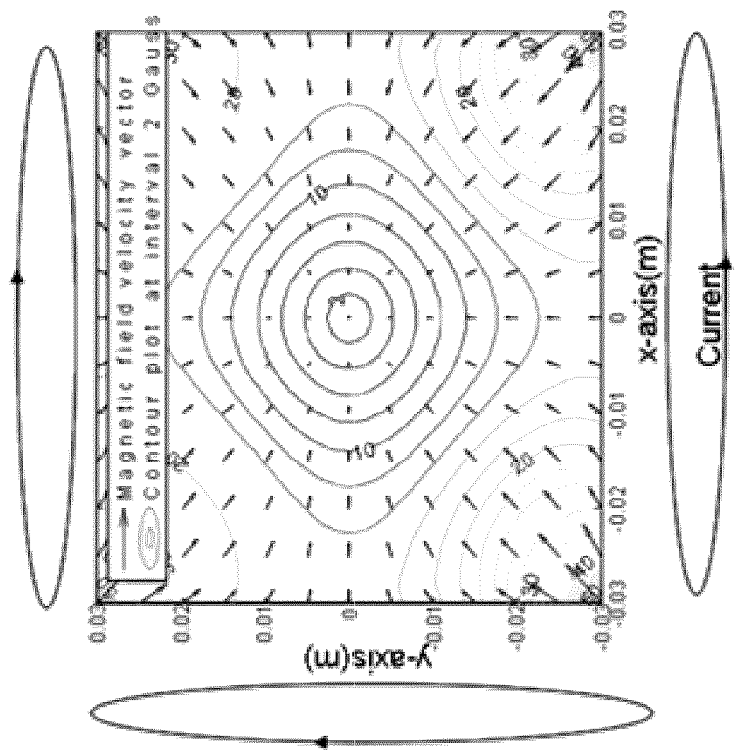
FIG. 4 is a planar magnetic field velocity vector generated from a 2D Maxwell pair (FIG. 4A); and Magnetic field absolute value as generated by a two sets of opposing Maxwell coil pairs in the x and y-axis.

Main Powering Sequences for SSPE Aggregation in a 3D Space. The resulting magnetic fields from the Maxwell pairs (opposite current in each coil of the same pair) is depicted in FIG. 4a and FIG. 4b for two orthogonal pairs. FIG. 4a shows the planar magnetic field velocity vector generated from a 2D Maxwell pairs. FIG. 4b shows magnetic field absolute value as generated by a two Maxwell coil pairs in the x and y-axis. The magnetic field lines are directed toward the center (the convergence point) where the field intensity is (near) zero (toward a minimum value). It will be appreciated that non-orthogonal coil geometries may nevertheless create a three dimensional convergence point.

Figure 5:
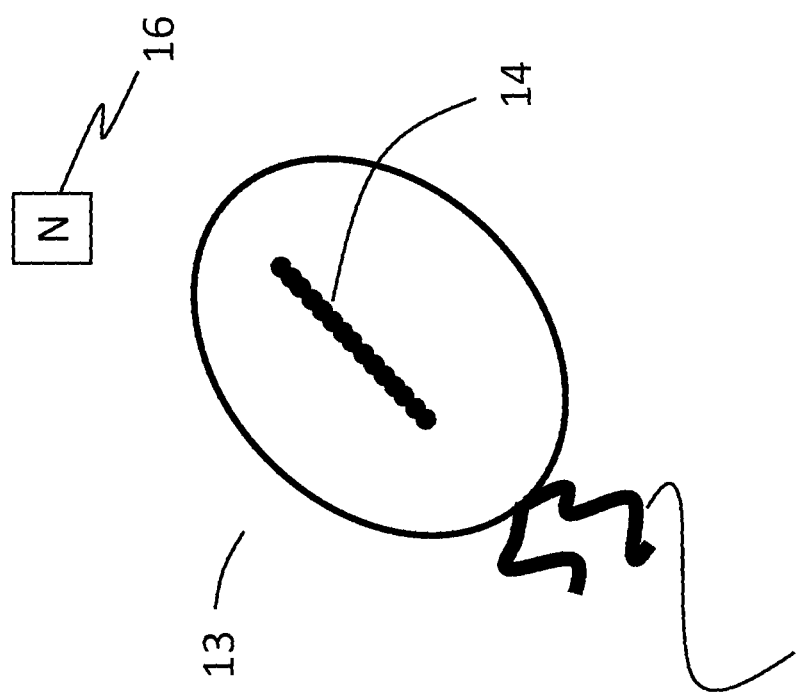
FIG. 5 (appearing on same sheet as FIG. 1) is an illustration of a cube with numbers for each edge to facilitate comprehension of directional current flow.

Whatever the location of the SSPE before applying the magnetic field, they will all be directed to the center (convergence point) after the magnetic field is applied (provided that the SSPE are initially located within the operational range of the magnetotaxis system). Notice also that an outer limit can also exist due to an undesirable motion behaviour of the SSPE in a higher intensity magnetic field. This plot is done for the 2D case. In order to apply the Maxwell magnetic field in 3D space, temporal multiplexing is required. In fact, each coil will have a longitudinal component of the magnetic field (the one required for SSPE trapping) and a transversal magnetic field. The transversal field from one coil is opposite to the longitudinal component of the transversal coils. Since the longitudinal component has higher amplitude than the transversal one, the resulting magnetic field will be sufficiently high for SSPE trapping. However, if three pairs are powered at the same moment, each direction will have a longitudinal component added to four transversal components, which will cause a close cancellation of the longitudinal field. In order to apply a Maxwell field in 3D, some powering sequences of the coils are possible in a time multiplexing fashion unless there is an obstacle preventing the "spreading" of the SSPE in at least one direction. The latter is a fundamental principle of the magnetotaxis system. Among the possible sequences, the coils can be powered by group of two pairs. Since there are 3 different combinations, each group of coils has to be powered typically ⅓ of the time period. Another alternative is to continuously power two pairs of the Maxwell coils and reversing the direction of the lines of magnetic fields produced by the remaining Maxwell pairs in a time multiplexed fashion. As mentioned previously, other sequences are also possible. The same idea of time-multiplexed sequences can be applied to other configurations. Throughout the examples provided hereinafter and in the embodiments shown in FIGS. 5 to 8, the X, Y and Z planes are defined as the following:

FIG. 5 is an illustration of a cube with numbers for each edge to facilitate comprehension of directional current flow. The X-axis is defined by an axis passing through coils arranged in the 1375 and 2486 configuration. It will be understood that 1375 defines one face of the cube (a square) represented by the 1, 3, 7 and 5 corners. As shown in FIG. 6, when the current in the X set of coils (X1 and X2) is said to be in the same direction (both X1 and X2 in direction D1), it will be understood current flows in a virtual coil in the direction 1, then 3, then 7, then 5, then 1, etc., in the X1 coil, and 2, then 4, then 8, then 6, then 2 etc., in the X2 coil. This configuration would create a Helmholtz or Maxwell like coil and a constant magnetic field in a plane than traverses the 1375 and 2486 sides of the cube. On the other hand, all other things being constant, if the current in the X2 coil is reversed (flow 2684 instead of 2486), the magnetic field generated by the opposing currents in the X1 and X2 coils would be oriented toward a middle point and this is understood to be currents in the opposite direction.

Y-axis is defined by an axis passing through coils arranged in the 1243 and 5687 configuration. It will be understood that 1243 defines a face of the cube (a square) represented by the 1, 2, 4 and 3 corners. When the current in the Y set of coils (Y1 and Y2) is said to be in the same direction (both Y1 and Y2 in direction D1), it will be understood current flows in a virtual coil in the direction 1, then 2, then 4, then 3, then 1, etc., in the Y1 coil, and 5, then 6, then 8, then 7, then 5 etc., in the Y2 coil. It will be understood by those skilled in the art that if current is in the same direction and both coils are reversed, the magnetic field will change directions and the same applies for the other planes.

Z-axis is defined by an axis passing through coils arranged in the 1265 and 3487 configuration. It will be understood that 1265 defines a face of the cube (a square) represented by the 1, 2, 6 and 5 corners. When the current in the Z set of coils (Z1 and Z2) is said to be in the same direction (both Z1 and Z2 in direction D1), it will be understood current flows in a virtual coil in the direction 1, then 2, then 6, then 5, then 1, etc., in the Z1 coil, and 3, then 4, then 8, then 7, then 3 etc., in the Z2 coil.

It will be understood by those skilled in the art that an AZ is created by the action of two opposing magnetic field sources in two planes. In the example below, the AZ is created by the action of sets of opposed magnetic field sources in the X and Y planes. It will be understood that, upon the action of the X and Y sources, the entities would aggregate in 2 axes (X,Y), while not "aggregating" in a third axis (Z). For example, in this case, creating a "circular" aggregation zone in the X an Y planes would cause a three dimensional AZ in the form of a "cylinder" because entities do not aggregate in the Z axis.

Figure 9:
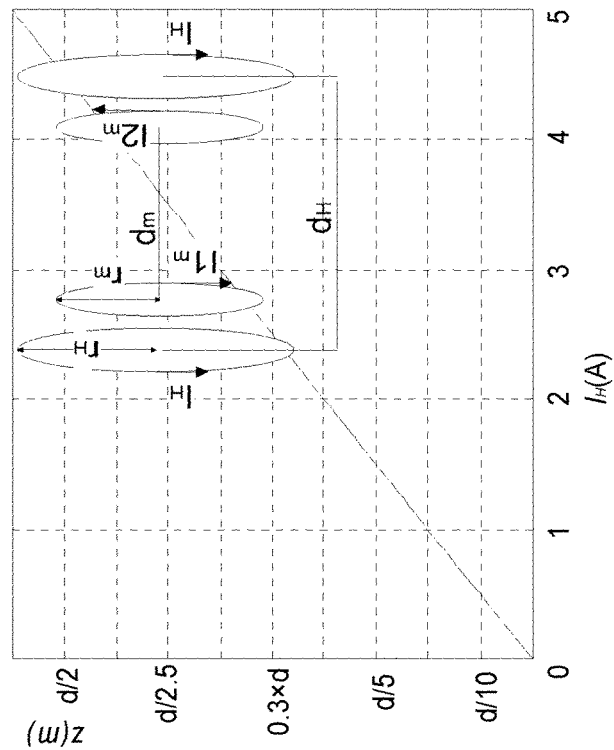
FIG. 9 (appearing on same sheet as FIG. 3) is a graphical representation showing the distance of a convergence point from a center point as a function of current ratio in two opposing Helmholtz coils and the displacement value of Maxwell magnetic fields.

Other configurations are also possible. To avoid the non-linearity for instance, the patient (ref.: Patient Mobility (PM) configuration) and/or coils (ref.: Coil Mobility (CM) configuration) could be physically moved instead, leading to a need to enlarge the inner diameter of the coil configuration to accommodate such displacements and hence, a need to increase the electrical energy to achieve the same results (i.e. induced directional torque value on the SSPE) as the preceding configuration. Other alternatives are possible. For instance, a combination of 3-axis Helmholtz coils 85 and 3-axis Maxwell coils 86 (ref.: HM configuration) can be implemented as depicted in FIG. 8 where the 3-axis Helmholtz coils 85 (shown as the lighter dotted pattern and where only one of the two opposing coils in that axis is identified) control the position of the magnetic field convergence point generated by the 3-axis of Maxwell coils 86 (shown as the darker dotted pattern and where only one of the two opposing coils in that axis is identified) leading as depicted in FIG. 9, in a linear (or quasi-linear) relationship between the current flowing in the Helmholtz coils and the position of the convergence point generated from the Maxwell pairs.

Figure 8:
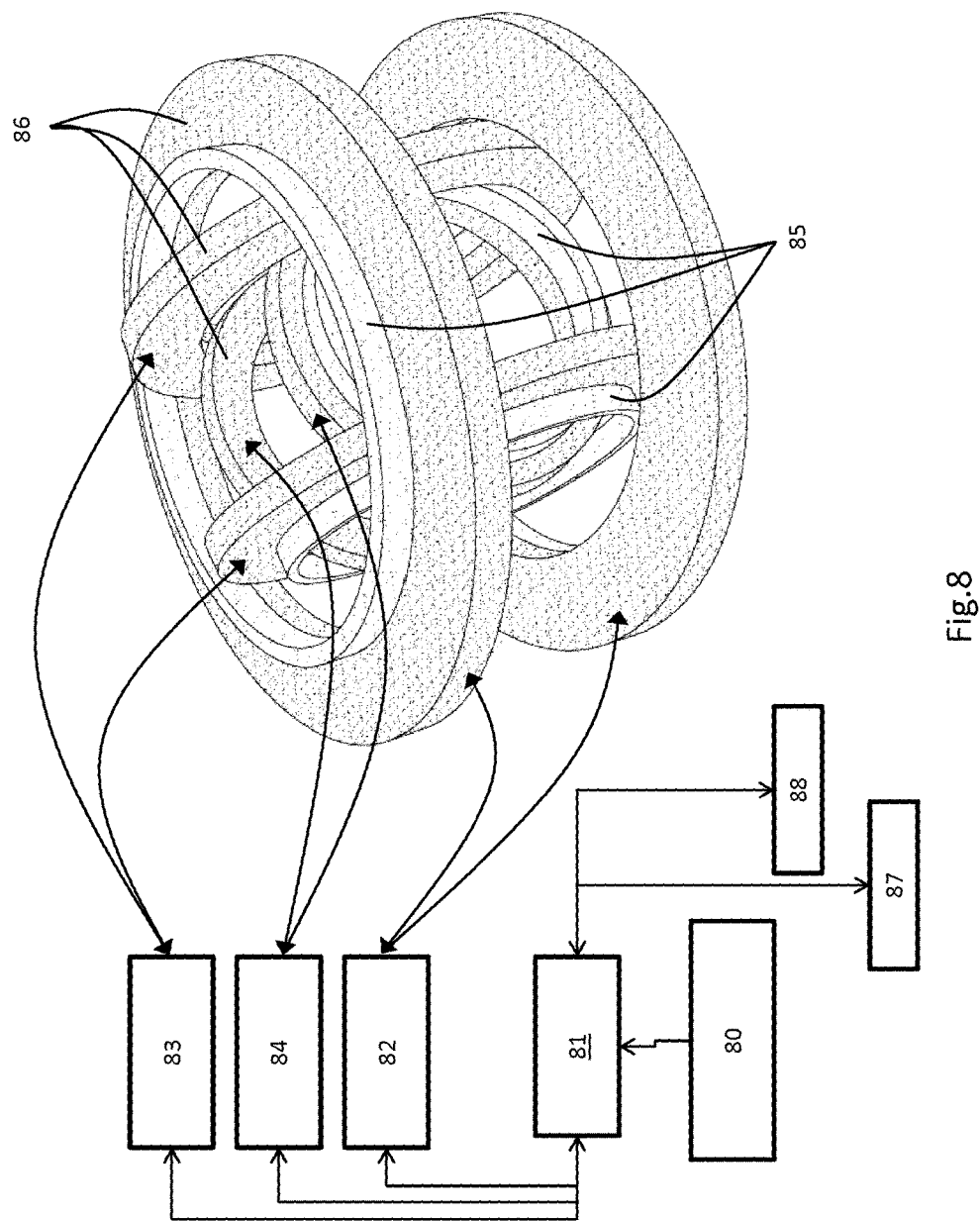
FIG. 8 is an embodiment of a coil configuration for implementation of a magnetotaxis system according to the present invention.

In FIG. 8, the controller 81 receives input from user interface 80 and sends output to each of three coil drives, such as the X coil drive 82 which independently controls the two opposing coils in the X-axis, the Y coil drive 83 which independently controls the two opposing coils in the Y-axis and the Z coil drive 84 which independently controls the two opposing coils in the Z-axis thus allowing the coils to generate magnetic field gradients thus acting as magnetic field sources. The coil drives 82,83,84 are shown to control only the Maxwell coils to simplify the illustration but it is understood that the controller can also control, if required, the Helmholtz coils 85. The controller 81 is configured to control the location of the convergence point 10 by controlling the current in each of the coils shown in FIG. 8 according to a predetermined program (see FIG. 19). The coil drives 82,83,84 can control the amount and direction of current in each of its two opposing coils in order to control the location of a convergence point 10. In some embodiments, the coil drives 82,83,84 control the location of the convergence point 10 using a position device (not shown) incorporated in the coil drives which is configured to receive input from the controller 81 and move the coils with respect to a platform 88 located inside the 3-axis coils (the platform 88 is shown outside the coils for simplicity). In use, a patient lies on the platform 88 that is or will be located inside the 3-axis coils. In other embodiments, the magnetic field sources (i.e. coils) are stationary and the platform 88 is moved to move a convergence point 10 to a different location inside the body. The controller 81 can receive input from a detector 87 about the location of a magneto-responsive entity in the body and the detector can be an MRI machine or PET-Scan machine.

Aggregation Zone. When operational, the SSPE are trapped (constrained) between the Maxwell coils in a region where they accumulate. The size of this region referred to here as the convergence point 10 depends on the intensity (magnitude) of the magnetic field as well as on the sensitivity (minimum magnitude of the directional magnetic field (gradient) to induce a torque on the SSPE sufficient for adequate directional control (magnetotaxis control). This sensitivity to the magnetic field depends on their magnetic moment which may vary among SSPE. When reaching this convergence point 10, the SSPE are relatively free to move in all directions until they reach a directional magnetic field with a magnitude sufficiently high to bring them to the AZ again. Hence, the convergence point 10 is defined here as mentioned earlier as the region where the magnetic field intensity induces negligible (meaning not sufficient to induce adequate directional control) directional torque on the SSPE used or selected for targeting purpose. The Helmholtz coils can offset the AZ created by the Maxwell magnetic field linearly (or quasi-linearly) in all directions in space. The aggregation zone 20 is understood to be larger than the convergence point 10 and the magnetic field in the AZ 20 tends to force the SSPEs toward the CP 10.

Other Configurations. As mentioned earlier, other configurations are also possible. For instance, with the previous configuration relying on pairs of Maxwell and Helmholtz coils, the result is like moving a magnetic tip under a plane and moving the aggregate of SSPE within the same plane using linear gradients or with non-linear gradients if the configuration is simplified with only Maxwell coils in this example. For medical interventions, the methods proposed here uses techniques (e.g. time-multiplexing) to operate similarly to a magnetic tip (permanent or electromagnet) that can be positioned in any plane inside the body or workspace.

Other variances are also possible especially when the target is accessible or exposed. In the latter case and depending on the region being targeted, the magnetic field could be generated at the end of a tool such as a stick or similar apparatus (e.g. a catheter). Nonetheless, in the latter case unlike the use of a coil configuration surrounding the target, targeting deeper from the accessible surface would be restricted if the convergence point is too deep and below the lower plane of the coil configuration.

The location of the magnetotaxis system with regard to the Magnetic Resonance Navigation (MRN) or an MRI system is also a concern if MRN operations or just MR imaging is used during the intervention. Ideally when used as a complementary system to the MRN (MRI) system, the magnetotaxis system should be installed close enough to the MRN or MRI system to facilitate registration and transfer (including reducing the transfer time) of the patient between the two platforms. Indeed, since SSPE cannot operate correctly in the high intensity homogeneous field of the MRN or MRI system, placing the magnetotaxis system far enough to the $B_0$ field so that it does not interfere with the proper operations of the SSPE is essential. On the other hand, the embedded steering of the SSPE (e.g. the superparamagnetic magnetosomes of the MC-1 bacteria) can be used to track (or locate) the SSPE using MRI techniques and as such, it should ideally be closed enough to the MRN or MRI system to ease the transfer of the patient (e.g. by an extension of the motion of the sliding table on which the patient is laid down) in order to monitor the progress of the SSPE using MRI techniques while facilitating the registration process. As an alternative, the distance separating the magnetotaxis system and the MRN system could be reduced further if a larger current in particular coils could be provided to compensate or correct for the influence of the $B_0$ field. Another option would be to add a coil, coils, or a shield (typically between the two platforms) to eliminate or reduce the effect of the $B_0$ field in the working zone of the magnetotaxis system. In some instances, the influence of the $B_0$ field could be exploited in the design of the magnetotaxis system (and by adjusting the parameters by varying the intensity of the electrical currents in specific coils of the magnetotaxis system and/or controlling the effect of the $B_0$ field by moving the magnetotaxis system closer or farther away from the MRN system). In all configurations mentioned above and others capable of the same functionalities, other configurations of magnetotaxis systems could rely on one or more coils being replaced by permanent magnets.

Portable and Hybrid Configurations. To avoid some potential issues such as registration or movement of the patient to name but only two examples that could cause errors in the accuracy of the positioning process of the convergence point in a specific targeted zone (e.g. in a tumoral region), a portable version of the magnetotaxis system may be desirable provided that the region to be targeted is accessible to such an instrument. Two examples where such portable version may be used is for targeting regions in the body made accessible after openings by surgery, by techniques such as laparoscopy, or for some cases of rectal or colorectal cancers, to name but only a few examples. In the latter case for example, a portable version of the magnetotaxis system can be introduced in the rectum 108 as depicted in FIG. 10. The advantage of this approach is that it is less sensitive to issues such as registration and the movement of the patient since the instrument (local coils or magnets) is positioned near or next to the targeted region after the injection of the SSPE which could be done by an injector embedded in the same instrument of by an independent instrument. The local coil configuration of the magnetotaxis instrument could be designed to change its shape or radius to better fit the shape of the tumor or a set of various portable magnetotaxis tools, each with a different diameter, could be provided. FIG. 10 shows an embodiment such a portable magnetotaxis system having a magnetotaxis probe 102 at the end of a tether 106. The probe 102 is inserted, in this example, through the rectum 108 to reach a tumor 104 target site. Once the probe 102 has reached the tumor 104, magnetic fields are generated to direct the magneto-responsive entities to the convergence point 10, which is located at or inside the tumour 104.

FIG. 11 shows an embodiment that allows for deeper targeting of the magnetotaxis system through the use of an external source of magnetic fields such as an external coil 114. The arrows represent the direction of the magnetic field where two arrows in opposite directions operate in a time-multiplexing mode. In this embodiment, the magnetotaxis probe 112 and tether 106 are inserted as in the portable configuration but instead of "encircling" the tumour with the probe 112, the opposed magnetic field source (external coil 114) is strategically located on the skin surface 116, outside the body, as close as possible to the target site.

When access is limited such as when the targeted region is located deeper in the colon for colorectal cancer treatments for instance, a magnetotaxis platform may be more appropriate since placing the source of magnetic fields of a portable version to the site considering the length of travel, the diameter of the colon and the weight of the coils may be difficult if possible or practical. As such a marker for registration purpose such as one placed at the tip of a catheter for example can be used instead in combination with the magnetotaxis platform (and using an imaging modality for real-time registration such as x-ray or CT).

Path Finding Capability. The modes of operation used depend if the magneto-responsive entity or SSPE 126 has embedded Path Finding capability or not. This is illustrated in FIG. 12 with a very simple example. The SSPE 126 without embedded path-finding capability is depicted in FIG. 12a. This will typically be the case for an artificial or synthetic SSPE 126 (although a bio-mimetic artificial SSPE 126 with some level of path-finding capability could potentially be implemented). When a directional magnetic field gradient 128 (or a sequence of sequential magnetic field gradients) is used to point in the desired direction of motion for the SSPE 126 (e.g. towards a target), the latter will move under the influence of the induced torque generated by the same directional field. When the SSPE reaches a sufficiently wide obstacle 124 (such as the wall depicted in FIG. 12a), the SSPE 126 will typically remain at the location represented by the white circle in FIG. 12a until the direction of the directional magnetic field gradient 128 is changed. The latter is referred to have no or 0% path-finding capability. But to know in which direction and when the magnetic field line must be changed, some minimum required feedback information must be gathered for such SSPE 126. For instance, if the target location 122 to the right and identified with a circled T must be taken by the SSPE 126, then the SSPE 126 must be navigated along a pre-defined path that will lead to this particular target location 122. FIG. 12A therefore shows a SSPE 126 without path-finding capability being stopped when directed towards the obstacle 124 (the thick white arrow indicates direction of the magnetic field or directional torque induced). It is understood by those skilled in the art that the SSPE 126 is actually a plurality of SSPEs that are aggregated at a convergence point 10.

FIG. 12B shows that an SSPE 126 with path-finding capability does not remain immobile but rather "searches" for a path that leads to the direction of the directional magnetic field gradient 128. In this case, there is a possibility that the target channel 122 location (identified with a circle T) will be reached without changing the direction of the magnetic field unlike in the case of a SSPE 126 without path-finding capability shown in FIG. 12A.

Although possible for larger channels (or blood vessels with larger diameters), the limitations imposed by the spatial resolution of medical imaging modalities prevent such gathering of image data of the tinier channels or blood vessels. Hence, classical navigational control approaches do not apply since a path or trajectory cannot be defined due to the impossibility of gathering the required image information.

In these cases, SSPE with embedded path-finding capability (the MC-1 magnetotactic bacteria (MTB) is one example) can be considered instead. As depicted in FIG. 12b, with a constant directional magnetic field gradient 128 of FIG. 12B, the SSPE will typically not remain immobile when reaching the obstacle 124 but rather "search or seek" for a path that will allow such SSPE to continue towards the direction of the magnetic field (or in an opposite direction if the SSPE is south-seeking instead of north-seeking). In this particular example with perfect symmetry and conditions on both sides, there may be a 50/50 probability that the SSPE takes the desired target location 122 or going in a specific direction (or tendency to go towards a specific direction) when encountering an obstacle 124 due to some particular characteristics of the SSPE (e.g. the direction of rotation of the flagella, etc.). In all cases, this will lead to a specific motion behaviour of the SSPE. Behavioural Navigation Control (BNC) or Behavioural Control (BC) in short is then defined here when such behaviour (including path-finding capability) is taken into account to control such SSPE 126 toward a specific target.

Figure 13:
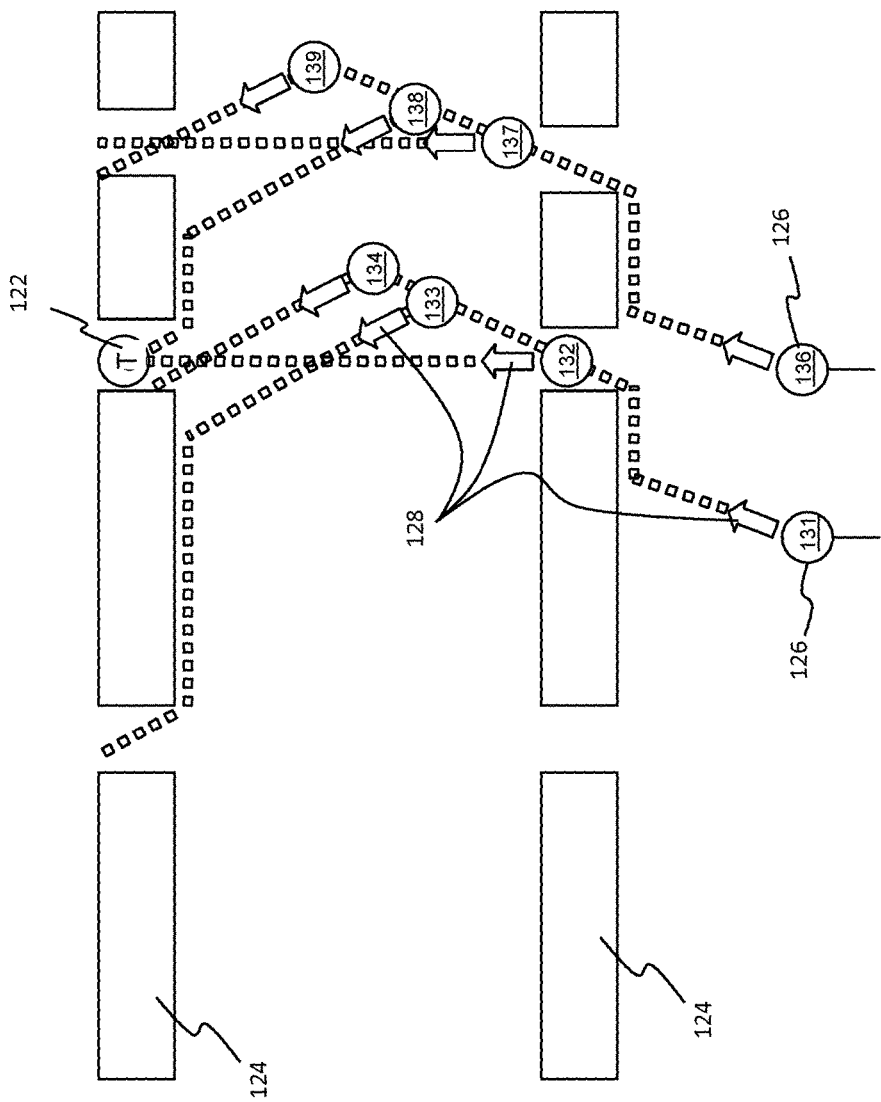
FIG. 13 shows an example of a directional mode applied to two pathfinding based (or non-path-finding in some instances if the angle from the obstacle is large enough) magneto-responsive entities showing some limitations of the method.

Directional versus Aggregation Mode. Considering the complexity of many navigable networks especially in environments such as the microvasculature or the angiogenesis network, relying on the behaviour of the path-finding-based SSPE alone may not be sufficient. To prevent or reduce the risk that such SSPEs take a wrong path that may lead to a final location outside the targeted area, changes in directional magnetic field alone without aggregation can be applied. This method referred to here as the directional mode is depicted in FIG. 13. This simple example shows that targeting efficacy using directional mode although very effective for many cases, can be very time-dependent as well as sensitive to the spatial distribution of the SSPE and to variations of their velocities. This is true even if real-time tracking and imaging the paths are possible (which is not true when operating in the microvasculature) as depicted in the following example.

In the example depicted in FIG. 13, two path-finding-based SSPEs 126 start at position 131 for SSPE A and position 136 for SSPE B. Both SSPEs are submitted to the same directional magnetic field gradient 128 (represented by thick white arrows) to bring SSPE A towards the intermediate targeted channel at position 132. When SSPE A is at position 132, the direction of the magnetic field is changed to direct SSPE A towards the final target identified by a circled T. Since the velocity of SSPE B is slightly higher than SSPE A in this particular example, SSPE B is at position 137 when the direction of the field is changed. In this case, only SSPE A will reach the target location 122 since SSPE B will enter the next adjacent channel in this particular case. FIG. 13 shows an example of directional mode applied to two path-finding-based (or non-path-finding) in some instances if the angle from the obstacle 124 is large enough) SSPEs showing some limitations of the method.

In another attempt, the change in directional field could be done later and compensated with a slight angle of the direction of the magnetic field. In this case and as depicted in FIG. 13, SSPE A could be at position 133 and SSPE B at position 138. Again, although SSPE B would reach the target, SSPE A would reach the adjacent channel at the left of the targeted channel. Waiting a bit longer such that SSPE A is at location 134 and SSPE B is at location 139 before changing the direction of the directional magnetic field gradient 128 would lead to the same result as the first attempt. Because of the initial positions of the SSPE, the geometry of the paths (obstacles 124) or characteristics of the environment, and the difference in velocities among the SSPE, only 50% targeting could be reached in this particular example even with real-time visual feedbacks. This number could be higher or lower in other cases but this simple example still demonstrate the limitations of the directional mode.

FIG. 14 is a highly schematic representation of a directional mode (D-mode) control of a plurality of magneto-responsive entities 151 or SSPEs that show a normal distribution with respect to "spreading". The white arrows represent the general direction of the magnetic field gradient used to direct the plurality of magneto-responsive entities 151. It can be observed that the spreading increases until the SSPEs reach an obstacle 124, after which point the regroup/concentrate, only to spread out again thereafter, until reaching the AZ 20.

To correct or improve for the aforementioned issues responsible for the limitations of the directional mode, the region where path-finding (PF) can be executed by the SSPE can be reduced (constrained) in an area defined earlier as the AZ 20 where all (or most) SSPEs 126 will initially converge to form an aggregate. This so-called aggregation mode is depicted in FIGS. 15-18. FIG. 15A shows use of the aggregation mode for targeting purpose; and FIG. 15B shows an example where a reduction of the AZ 20 is used to enhance the efficacy in targeting. As shown in FIG. 15A, both SSPEs will converge towards location A which would not be possible in this particular case using the directional mode alone. Initially, prior to aggregation within the AZ 20 shown as a circle with four hatched arrows pointing towards its center or Convergence Point 10, the two SSPEs are directed towards the convergence point 10 of the aggregation zone 20 by a directional magnetic field pointing toward the convergence point 10 that has a higher magnitude (shown in FIG. 14 with larger arrows than the hatched arrows at the periphery of the AZ) than the directional torque sensitivity of the SSPEs. When outside the periphery of the aggregation zone 20, the two SSPE will move in a straight or quasi-straight line toward the convergence point. Once they pass the periphery of an AZ 20, the directional torque will become less sufficient to maintain the directional movement of the SSPE toward the convergence point 10 of the 20. This will lead to more "random" or non-linear and uncontrolled directional motions (displacements) of the SSPE within the AZ 20. By waiting for a sufficient period of time until all SSPE have the time to reach the AZ 20, factors such as dependency to time, variation in velocities, and initial location of the SSPE will have no or substantially less impact unlike for the directional mode, on the efficacy in targeting. For example, changing the convergence point of the AZ 20 to the target 122 location represented by a T in FIG. 15a would result in 100% targeting efficacy in this particular case.

Nonetheless, the dimensions (e.g. diameter for a symmetrical AZ 20) of the AZ 20 should be adjusted appropriately. For instance, in the example of FIG. 15B, an AZ 20 with a diameter similar to the one in FIG. 15a would not yield the same targeting efficacy. In this case, some SSPE in the AZ could be directed towards the wrong channel and reach the wrong target location 153 instead of the target location 122. To avoid this, the dimensions of the AZ can be reduced with regard to the geometrical features of the environment (such as expected channel's widths and inter-channel separations). This is shown in FIG. 15B by the small black circle surrounded by four hatched arrows pointing toward its center. With this new small aggregation zone 155, 100% targeting efficacy can be achieved in this particular case. But this is paid by a higher power requirement for the magnetotaxis system.

Notice that in FIG. 15B, the AZ used for the target is larger than the preceding one. In this case, the obstacles 124 (walls, etc.) or geometrical features are used to constrain the SSPE instead of reducing the size of the AZ. When the exact geometrical features are not known in a specific region but the limits in geometrical features, the size of the AZ is typically adjusted accordingly.

Figure 17:
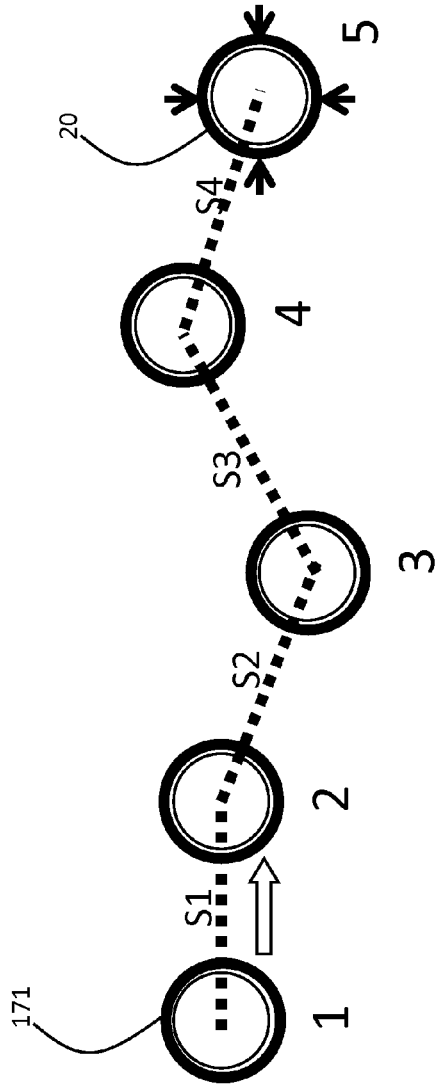
FIG. 17 is a schematic representation of an aggregation segmentation mode (S-mode) control of magneto-responsive entities.
Figure 18:
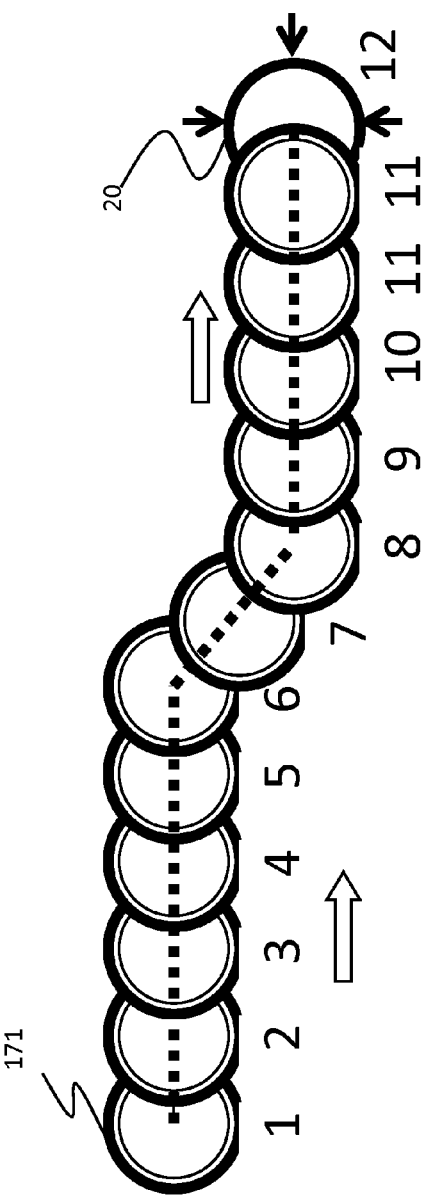
FIG. 18 is a schematic representation of an aggregation continuous mode (C-mode) control of magneto-responsive entities.

Aggregation Modes. There are three fundamental aggregation modes as depicted in FIGS. 16-18. The first one being also the simplest is referred to as the target mode or T-mode and is shown in FIG. 16. For the T-mode, the AZ 20 is simply maintained at the target location 122 during the whole operation until a predetermined amount or percentage of SSPEs 126 has reached the target site. It will be appreciated that the target location 122 can be a convergence point 10 inside an AZ 20, but this need not necessarily be the case. In some situations, the SSPE 126 can reach a point at which it can no longer follow magnetic fields, such as, for example, if it is stuck in a blood vessel that is smaller than its own diameter. In such cases, there is no need to create an AZ 20. It will also be appreciated that, in some cases, the target location 122 is the convergence point 10 but once again, this need not necessarily be the case.

The second aggregation mode is referred to as the segmentation mode or S-mode and is shown in FIG. 17. This mode takes into account the level of path-finding of the SSPE and the expected path geometry. This mode applies one (level 1 segmentation mode or S1-mode) or more (level 2 or S2-mode and up segmentation mode) intermediate AZ at different time between the SSPE injection site or initial aggregation zone 171 (or the site when this mode becomes operational) and the target AZ 20 (or the site when this mode ends). The position of the intermediate AZ is typically changed when all SSPE (or most of the SSPE) have reached that AZ. The last AZ 20 is the one at the targeted location 122. This mode may be useful compared to the target mode when the distance to travel is relatively long and the routes are chaotic or complex such that there is an important risk of losing a significantly large percentage of SSPE during travel or to being jammed in one location due to vessels geometries. An example of avoiding the latter case in a microfluidic channels using the C-mode with MC-1 MTB acting as SSPEs. As shown in FIG. 17, the aggregation zone is moved sequentially from 1 to 2 to 3 to 4 and to 5 while the segments between the aggregation zones are shown as S1 to S4. In this mode, the aggregation zones do not overlap and the SSPEs may not sense any magnetic field gradient at some point in the inter-zone segments (S1 to S4). In some embodiments, this is useful for travelling in large blood vessels where blood flow alone can move the SSPEs along the blood vessel.

The third aggregation mode is referred to as the continuous mode or C-mode and is shown in FIG. 18. With this mode, the AZ that contains the SSPE is moved between the initial aggregation zone 171 (or the site when this mode becomes operational) and the target AZ 20 (or the site when this mode ends) at a sufficiently low speed required to maintain the SSPE within the AZ. The AZ is sequentially moved from 1 to 12 (the target aggregation zone) but the sequential zones overlap such that, as opposed to the segmentation mode shown in FIG. 17, the SSPEs always sense a predetermined magnetic field gradient.

In all cases, a combination of the above modes can also be used. It should be noted that in the continuous mode or when operating inside the AZ, because the path-finding-capable SSPEs such as the MC-1 bacteria would have more freedom in directional motion by being less affected by the induction of a directional torque on the chain of magnetosomes embedded in the cell, may affect the efficacy in path finding compared to when operating outside the AZ.

Modulation Modes. There are different levels of path-finding capability for SSPE. For example, a simple hypothetic artificial sphere with a propelling system and a steering system passively oriented with a directional torque from a direction magnetic field may have 0% path-finding capability. On the other hand, for a SSPE with 100% path-finding capability, using the T-mode only would lead to 100% targeting efficacy independently of the complexity and geometrical features of the paths leading to the targeted region. Unfortunately, 100% path-finding capability is presently hypothetical and practically, path-finding-capable SSPE would be rated below 100%. As such, modulating the magnetic field becomes very important to enhance targeting efficacy in order to navigate the SSPE in problematic pathways taking into account the geometry of the channels, the SSPE speeds and behaviour for a given magnetic field intensity. For example, the motion behaviour of the MC-1 bacteria is different near obstacles as depicted in FIG. 15 which may improve targeting effectiveness. The magnitude of the magnetic field also has an impact on their motion behaviour and this can also be taken into consideration for the choice of an appropriate modulation mode and its associate settings.

But when the level of path-finding capability of the SSPE is not sufficient to reach the AZ or to achieve a sufficiently high targeting efficacy due to the geometry of the path between the present location of the SSPE and the targeted AZ, one or more modulation modes can be used in conjunction with the preceding aggregation modes.

There are four fundamental modulation modes namely, the amplitude modulation (AM) mode, the offset modulation (OM) mode, frequency modulation (FM) mode, and shape modulation (SM) mode where each mode can operate at different frequencies. As mentioned earlier, these four fundamental modulation modes typically work in conjunction with one or more of the four fundamental aggregation modes mentioned in the previous section.

For instance, for the T-AM mode, the diameter of the AZ is modulated in amplitude (i.e. that the overall size of the AZ is changed back-and-forth) at a specific frequency. Here, not only the amplitudes or changes in size of the AZ must be specified but also the frequency at which these changes occur. Although two sizes are typically used, more can be used in this mode.

Although FIG. 6 is not to scale, it shows that, by using higher gradients or current amplitude, a smaller convergence point 60 can be provided (or smaller AZ). This modulation technique is controlled by the controller 81 and can help the bacteria or SSPE 126 to avoid obstacles 124 and hence increase targeting efficacy using the SSPEs 126 inherent pathfinding capability. In another example where the convergence point needs to be moved toward the left side coil (X1) to a location shown as the dashed circle location 61 in order to avoid an obstacle 124, the controller 81 is configured to control the current, direction, actuation of the four coils shown as X1, X2, Y1 and Y2 in order to cause the convergence point 10 to be at the dashed circle location 61.

The same idea also holds true for the other modes. For instance, for the T-OM mode, the convergence point of the AZ positioned at the target is shifted between the center of the targeted zone and one or more shifted positions at one or more specific distances and frequencies. As for the T-FM mode, the current in the magnetotaxis system is simply turned on and off and a specified frequency. Finally for the T-SM, the shape is changed between, for example the shape of convergence point 10 and the switched to first shape 71 or second shape 72 two shapes) at a specified frequency. An example is depicted in FIG. 7.

The basic idea of the various types of modulation modes is to slightly change the direction of the SSPE to avoid being blocked along the way by an obstacle. Although the magnetotactic bacteria can swim around obstacles, they cannot go around some types of obstacles along the way if we do not slightly help them by forcing them to look around for an exit point. This is what the modulation is doing. Such modulation modes can be applied accordingly to a priori knowledge (models) of the capillary network for instance, etc. If you change the size of the AZ, the direction of the magnetic field line converging to the convergence point will slightly change direction, this is the amplitude modulation. Instead of changing the overall size of the AZ, you can change its shape, this will result also in a slight change in the direction towards the convergence point, and this is the shape modulation. You can also displace the convergence point to achieve a change in the directional convergence magnetic field lines; this is referred to as the offset modulation. For the frequency modulation, the system is turned on and off at a specific frequency. When the system is off (no current circulating in the coils), there will be no directional torque on the chain of magnetosomes if using magnetotactic bacteria as SSPE, therefore the bacteria will go randomly which may help getting out of a vascular cul-de-sac, then we turn on again to direct them toward the tumor or other target before they go too far off track. All of these modulation modes can be combined in order to better control targeting, aggregation and path-finding of the SSPEs.

Figure 19B:
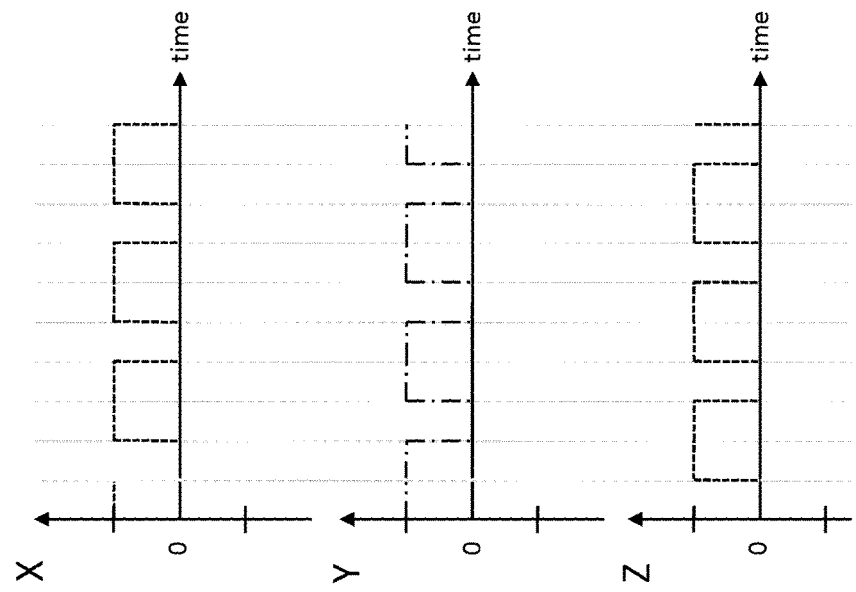
FIG. 19A represents a first predetermined program and FIG. 19B represents a second and different predetermined program to generate a 3-dimensional convergence point.
Figure 19A:
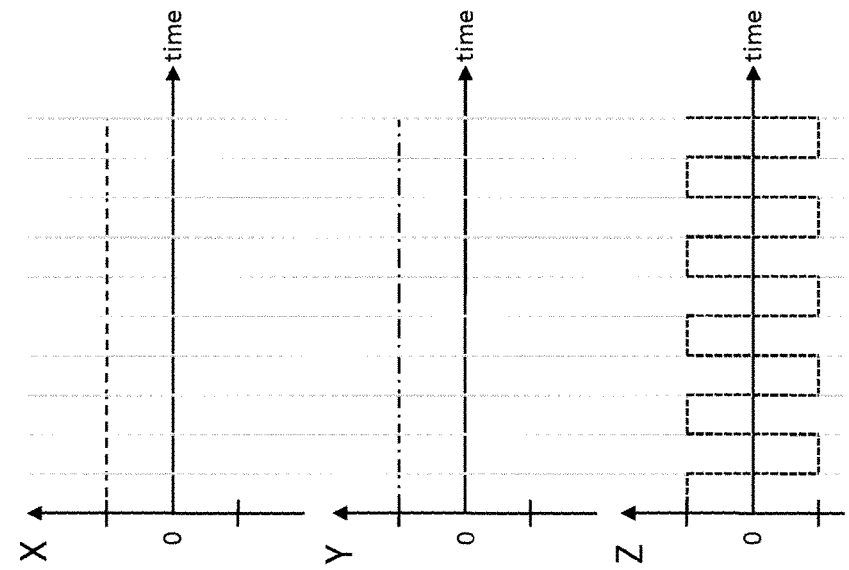

FIG. 19 is a graphical representation of predetermined programs (e.g. time-multiplexing) for generating a convergence point using opposing sets of coils arranged in the X, Y and Z axes, where FIG. 19A represents a first predetermined program and FIG. 19B represents a second and different predetermined program to generate a 3-dimensional convergence point 10. In FIG. 19A, it will be appreciated that, for the X-axis coils, the pair of opposing and generally parallel coils (using the nomenclature found in FIG. 6) that generate a magnetic field gradient in the X-axis receives a certain current in each coil (X1 and X2) and the currents flow in opposed directions (D1 and D2) in the coils. As for the Y-axis coils, the pair of opposing and generally parallel coils that generate a magnetic field gradient in the Y-axis receives a certain current in each coil (Y1 and Y2) and the currents flow in opposed directions (D1 and D2) in the coils. Finally, the opposing set of coils in the Z-axis receives a certain current which flows in a same direction (D1 only) in both coils and that direction is reversed in both coils according to a predetermined frequency.

FIG. 19B represents an alternate time-multiplexing program for generating a three dimensional convergence point using combinations of two sets of coils at a time (e.g. X and Y) while a third set (e.g. Z) is inactive (i.e. a sequence in which the magnetic field source does not generate a magnetic field gradient in the Z-axis). It will be understood that all possible combinations of two sets of magnetic field sources in the X, Y and Z axes are the following: (X,Y); (X,Z); (Y,Z).

Although the Maxwell configuration of coils is understood to be 3 parallel coils on a virtual sphere wherein each of the outer coils has a radius of square root (4/7)R and a distance of square root of (3/7)R from the plane of the central coil, with R being the central coil radius. It will be understood that, in an embodiment of the coil configuration where a parallel set of coils at a predetermined distance is provided, current flowing through both "opposed" coils should be in opposite directions (or reversed directions) in order to generate magnetic field gradients that cause aggregation of the SSPEs at a specific "central" location, where the magnetic field force is almost non-existent. The Helmholtz configuration is understood to mean two generally opposing and generally parallel coils where current flows in a same direction in order to generate a linear magnetic field gradient in one direction, while a Maxwell configuration is understood to mean two generally opposing and generally parallel coils where current flows in opposite directions in order to generate a convergence point at location between the coils that is dependent on the current flowing in each coil.

The term "body" should be interpreted in the broad sense. In an embodiment, body is a human body while in other embodiments, body could also be that of an animal or any physical object which could benefit from the aggregation (and targeting) of magneto-responsive entities. It will also be understood that the apparatus and method of the present invention are useful for using on cadavers for training and development purposes to purposes.

In some embodiments, the magneto-responsive entities are aggregated at a specific location in the human body for diagnostic purposes because some diagnostic compounds are more effective with a localized and highly specific delivery and/or toxic at high concentrations.

It will be understood by those skilled in the art that, in some embodiments, the body can be positioned inside the magnetic field sources or the magnetic field sources can be positioned around the body. Although a platform for receiving and immobilizing the patient with respect to the magnetic field sources is preferred, it is also possible to immobilize the magnetic field sources with respect to a body without a platform, such as with a person/body standing inside the magnetic field sources. A positioning system for positioning the magnetic field sources with respect to the body is advantageous. In some cases, the magnetic field sources are moved and in other cases, the body (on a platform or not) is moved. In both cases, registration of the body with respect to the magnetic field sources is advantageous for targeting entities to a specific convergence point. It is understood that, when the magnetic field source is a coil(s), it is of sufficient size to receive the body within the coil(s) in order to target the convergence point to any location inside the human body, including the head. In some embodiments, the apparatus in which the patient is placed comprising means, such as mechanical means, for positioning the coils around a body and means for releasing said body form the coils. In other embodiments, the patient/body is placed on a platform (chair, gurney, bed) and the platform is moved into the apparatus. In yet other embodiments, the platform is already located in the apparatus and the apparatus comprises further means for positioning the patient/body on the platform.

While the invention has been described in connection with specific embodiments thereof, it will be understood that it is capable of further modifications and this application is intended to cover any variations, uses, or adaptations of the invention following, in general, the principles of the invention and including such departures from the present disclosures as come within known or customary practice within the art to which the invention pertains and as may be applied to the essential features herein before set forth, and as follows in the scope of the appended claims.

What is claimed is:

1. A method of treating a patient using magnetotactic bacteria comprising:
   introducing therapeutic agent-carrying magnetotactic bacteria to a patient;
   inserting in said patient and positioning, at a location in proximity to or at a treatment site, a probe capable of generating a magnetic field, wherein said magnetic field is sufficient to induce a directional torque that influences said magnetotactic bacteria;
   allowing said magnetotactic bacteria to move to and aggregate at or near said probe;
   delivering said therapeutic agent, carried by said magnetotactic bacteria, at said treatment site; and
   removing said probe from said patient.

2. The method as defined in claim 1, wherein said treatment site is a site of a tumor.

3. The method as defined in claim 2, wherein said probe is inserted in a rectum of said patient to reach said site of said tumor.

4. The method as defined in claim 2, wherein said probe is inserted in an opening made in said patient during a surgery.

5. The method as defined in claim 1, wherein said magnetotactic bacteria are introduced at said location of insertion of said probe.

6. The method as defined in claim 5, wherein said probe comprises an injector configured to introduce said magnetotactic bacteria to said patient, and wherein said introducing said magnetotactic bacteria is performed using said injector of said probe.

7. The method as defined in claim 1, further comprising adapting the shape of said probe as a function of properties of said treatment site.

8. The method as defined in claim 1, further comprising placing a magnetic field source outside of the body of said patient to generate an additional magnetic field to further direct said magnetotactic bacteria to said treatment site.

9. The method as defined in claim 8, wherein said magnetic field source is placed on the surface of skin of said patient in proximity to said treatment site.

* * * * *